United States Patent
Dugan

(10) Patent No.: US 8,947,226 B2
(45) Date of Patent: Feb. 3, 2015

(54) BANDS FOR MEASURING BIOMETRIC INFORMATION

(76) Inventor: Brian M. Dugan, Sleepy Hollow, NY (US)

( * ) Notice: Subject to any disclaimer, the term of this patent is extended or adjusted under 35 U.S.C. 154(b) by 194 days.

(21) Appl. No.: 13/488,436

(22) Filed: Jun. 4, 2012

(65) Prior Publication Data

US 2012/0306643 A1 Dec. 6, 2012

Related U.S. Application Data

(60) Provisional application No. 61/493,313, filed on Jun. 3, 2011.

(51) Int. Cl.
| | | |
|---|---|---|
| G08G 1/08 | (2006.01) | |
| A61B 5/0205 | (2006.01) | |
| A61B 5/02 | (2006.01) | |
| A61B 5/00 | (2006.01) | |

(52) U.S. Cl.
CPC .............. *A61B 5/0205* (2013.01); *A61B 5/02* (2013.01); *A61B 5/6813* (2013.01)
USPC .................. 340/539.1; 340/539.12; 340/10.1; 455/41.2; 455/466; 600/301

(58) Field of Classification Search
CPC ...... A61B 5/0002; A61B 5/02; A61B 5/0245; A61B 5/1118; A61B 5/681
USPC ............ 340/539.12, 539.1, 573.1, 5.82, 10.1; 600/500, 300, 301; 455/4.9, 420, 466, 455/41.2, 41.3
See application file for complete search history.

(56) References Cited

U.S. PATENT DOCUMENTS

| | | |
|---|---|---|
| 3,834,702 A | 9/1974 | Bliss |
| 4,484,743 A | 11/1984 | Williams |
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,142,358 A | 8/1992 | Jason |
| RE34,728 E | 9/1994 | Hall-Tipping |
| 5,362,069 A | 11/1994 | Hall-Tipping |
| 5,377,100 A | 12/1994 | Pope et al. |
| 5,462,504 A | 10/1995 | Trulaske et al. |
| 5,515,865 A | 5/1996 | Scanlon |
| 5,527,239 A | 6/1996 | Abbondanza |
| 5,591,104 A | 1/1997 | Andrus et al. |
| 5,592,401 A | 1/1997 | Kramer |
| 5,624,316 A | 4/1997 | Roskowski et al. |
| 5,645,513 A | 7/1997 | Haydocy et al. |
| 5,667,459 A | 9/1997 | Su |
| 5,672,107 A | 9/1997 | Clayman |
| 5,702,323 A | 12/1997 | Poulton |
| 5,781,698 A | 7/1998 | Teller et al. |
| 5,885,156 A | 3/1999 | Toyohara et al. |
| 5,902,250 A | 5/1999 | Verrier et al. |
| 5,918,603 A | 7/1999 | Brown |

(Continued)

FOREIGN PATENT DOCUMENTS

| | | |
|---|---|---|
| EP | 1 292 217 B1 | 11/2005 |
| EP | 1 639 939 A1 | 3/2006 |

(Continued)

OTHER PUBLICATIONS

Dugan et al., U.S. Appl. No. 13/898,437, filed May 20, 2013.

(Continued)

*Primary Examiner* — Steven Lim
*Assistant Examiner* — Hongmin Fan
(74) *Attorney, Agent, or Firm* — Dugan & Dugan, PC

(57) ABSTRACT

In some aspects, a system is provided that includes (1) a wrist band having one or more sensors that measure biometric data of a user wearing the band; and (2) a display on the band that displays a message based on biometric data measured by the band. The message indicates a heart rate zone of the user. Numerous other aspects are provided.

22 Claims, 5 Drawing Sheets

(56) References Cited

U.S. PATENT DOCUMENTS

| | | |
|---|---|---|
| 5,928,133 A | 7/1999 | Halyak |
| 5,947,868 A | 9/1999 | Dugan |
| 6,024,675 A | 2/2000 | Kashiwaguchi |
| 6,062,216 A | 5/2000 | Corn |
| 6,066,075 A | 5/2000 | Poulton |
| 6,152,856 A | 11/2000 | Studor et al. |
| 6,179,713 B1 | 1/2001 | James et al. |
| D439,981 S | 4/2001 | Kasabach et al. |
| 6,213,872 B1 | 4/2001 | Harada et al. |
| 6,244,988 B1 | 6/2001 | Delman |
| 6,251,010 B1 | 6/2001 | Tajiri et al. |
| 6,267,677 B1 | 7/2001 | Tajiri et al. |
| 6,302,789 B2 | 10/2001 | Harada et al. |
| D451,604 S | 12/2001 | Kasabach et al. |
| 6,347,993 B1 | 2/2002 | Kondo et al. |
| 6,354,940 B1 | 3/2002 | Itou et al. |
| 6,375,572 B1 | 4/2002 | Masuyama et al. |
| D460,971 S | 7/2002 | Sica et al. |
| 6,456,749 B1 | 9/2002 | Kasabach et al. |
| 6,482,092 B1 | 11/2002 | Tajiri et al. |
| 6,494,830 B1 | 12/2002 | Wessel |
| 6,513,160 B2 | 1/2003 | Dureau |
| 6,514,199 B1 | 2/2003 | Alessandri |
| 6,527,711 B1 | 3/2003 | Stivoric et al. |
| 6,579,231 B1 | 6/2003 | Phipps |
| 6,585,622 B1 | 7/2003 | Shum et al. |
| 6,595,858 B1 | 7/2003 | Tajiri et al. |
| 6,595,929 B2 | 7/2003 | Stivoric et al. |
| 6,605,038 B1 | 8/2003 | Teller et al. |
| 6,628,847 B1 | 9/2003 | Kasabach et al. |
| 6,641,482 B2 | 11/2003 | Masuyama et al. |
| 6,652,383 B1 | 11/2003 | Sonoda et al. |
| 6,705,972 B1 | 3/2004 | Takano et al. |
| 6,720,983 B1 | 4/2004 | Massaro et al. |
| 6,746,371 B1 | 6/2004 | Brown et al. |
| 6,758,746 B1 | 7/2004 | Hunter et al. |
| 6,786,825 B2 | 9/2004 | Kawazu |
| 6,796,927 B2 | 9/2004 | Toyama |
| 6,881,176 B2 | 4/2005 | Oishi et al. |
| 6,888,779 B2 | 5/2005 | Mollicone et al. |
| 6,902,513 B1 | 6/2005 | McClure |
| 6,966,837 B1 | 11/2005 | Best |
| 7,020,508 B2 | 3/2006 | Stivoric et al. |
| 7,041,049 B1 | 5/2006 | Raniere |
| 7,057,551 B1 | 6/2006 | Vogt |
| 7,068,860 B2 | 6/2006 | Kasabach et al. |
| 7,153,262 B2 | 12/2006 | Stivoric et al. |
| 7,261,690 B2 | 8/2007 | Teller et al. |
| 7,285,090 B2 | 10/2007 | Stivoric et al. |
| 7,628,730 B2 | 12/2009 | Watterson et al. |
| 7,749,056 B2 | 7/2010 | Ando et al. |
| 7,931,563 B2 | 4/2011 | Shaw et al. |
| 7,934,983 B1 | 5/2011 | Eisner |
| 7,946,959 B2 | 5/2011 | Shum et al. |
| 8,188,868 B2 | 5/2012 | Case, Jr. |
| 8,287,436 B2 | 10/2012 | Shum et al. |
| 8,313,416 B2 | 11/2012 | Ellis et al. |
| 2002/0022516 A1 | 2/2002 | Forden |
| 2002/0080035 A1 | 6/2002 | Youdenko |
| 2002/0082065 A1 | 6/2002 | Fogel et al. |
| 2002/0082077 A1 | 6/2002 | Johnson et al. |
| 2002/0090985 A1 | 7/2002 | Tochner et al. |
| 2002/0151992 A1 | 10/2002 | Hoffberg et al. |
| 2002/0160883 A1 | 10/2002 | Dugan |
| 2002/0163495 A1 | 11/2002 | Doynov |
| 2003/0224337 A1 | 12/2003 | Shum et al. |
| 2004/0003133 A1* | 1/2004 | Pradhan et al. ............... 709/318 |
| 2004/0023761 A1 | 2/2004 | Emery |
| 2004/0053690 A1 | 3/2004 | Fogel et al. |
| 2005/0068169 A1 | 3/2005 | Copley et al. |
| 2005/0101845 A1 | 5/2005 | Nihtila |
| 2005/0177051 A1 | 8/2005 | Almen |
| 2005/0275541 A1 | 12/2005 | Sengupta et al. |
| 2006/0025282 A1 | 2/2006 | Redmann |
| 2006/0031102 A1 | 2/2006 | Teller et al. |
| 2006/0089543 A1 | 4/2006 | Kim et al. |
| 2006/0122474 A1 | 6/2006 | Teller et al. |
| 2006/0224051 A1 | 10/2006 | Teller et al. |
| 2006/0264730 A1 | 11/2006 | Stivoric et al. |
| 2006/0281543 A1 | 12/2006 | Sutton et al. |
| 2007/0004482 A1 | 1/2007 | Ando et al. |
| 2007/0038038 A1 | 2/2007 | Stivoric et al. |
| 2007/0053513 A1 | 3/2007 | Hoffberg |
| 2007/0111858 A1 | 5/2007 | Dugan |
| 2007/0167204 A1 | 7/2007 | Lyle et al. |
| 2007/0173705 A1 | 7/2007 | Teller et al. |
| 2007/0197274 A1 | 8/2007 | Dugan |
| 2007/0208233 A1 | 9/2007 | Kovacs |
| 2007/0260482 A1 | 11/2007 | Nurmela et al. |
| 2008/0027337 A1 | 1/2008 | Dugan et al. |
| 2008/0094226 A1 | 4/2008 | O'Shea et al. |
| 2008/0129518 A1 | 6/2008 | Carlton-Foss |
| 2008/0146892 A1 | 6/2008 | LeBoeuf et al. |
| 2008/0167861 A1 | 7/2008 | Inoue et al. |
| 2008/0191864 A1 | 8/2008 | Wolfson |
| 2008/0218310 A1 | 9/2008 | Alten et al. |
| 2008/0281633 A1 | 11/2008 | Burdea et al. |
| 2008/0318679 A1 | 12/2008 | Tran et al. |
| 2009/0005140 A1 | 1/2009 | Rose et al. |
| 2009/0054751 A1* | 2/2009 | Babashan et al. ............. 600/324 |
| 2009/0121894 A1 | 5/2009 | Wilson et al. |
| 2009/0270743 A1 | 10/2009 | Dugan et al. |
| 2010/0033303 A1 | 2/2010 | Dugan et al. |
| 2010/0160041 A1 | 6/2010 | Grant et al. |
| 2010/0240458 A1 | 9/2010 | Gaiba et al. |
| 2010/0287011 A1 | 11/2010 | Muchkaev |
| 2011/0065504 A1 | 3/2011 | Dugan et al. |
| 2011/0082008 A1 | 4/2011 | Cheung et al. |
| 2011/0121950 A1* | 5/2011 | Izadi et al. ................... 340/10.5 |
| 2011/0190055 A1 | 8/2011 | Leyvand et al. |
| 2011/0260830 A1 | 10/2011 | Weising |
| 2011/0275483 A1 | 11/2011 | Dugan et al. |
| 2012/0208676 A1 | 8/2012 | Shum et al. |
| 2012/0252580 A1 | 10/2012 | Dugan |
| 2012/0253487 A1 | 10/2012 | Dugan |
| 2012/0253489 A1 | 10/2012 | Dugan |

FOREIGN PATENT DOCUMENTS

| | | |
|---|---|---|
| EP | 1 292 218 B1 | 4/2006 |
| EP | 1 702 560 A1 | 9/2006 |
| EP | 1 743 571 A2 | 1/2007 |
| JP | 59-170173 | 9/1984 |
| JP | 08103568 | 4/1996 |
| WO | WO 96/05766 | 2/1996 |
| WO | WO 01/96986 A2 | 12/2001 |
| WO | WO 02/00111 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |
| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 | 10/2005 |

OTHER PUBLICATIONS

Busch, Fritz "Diabetes Institute Brings Dakota, New Ulm Together" Jun. 10, 2001. Ogden Newspapers, Inc.

"Bluetooth." Wikipedia: The Free Encyclopedia. Aug. 10, 2009 <http://en.wikipedia.org/wiki/Bluetooth>.

Ichinoseki-sekine et al., "Improving the Accuracy of Pedometer Used by the Elderly with the FFT Algorithm," Medicine & Science in Sports & Exercise 2006, 1674-1681.

Mann, W. et al., "Smart Phones for the Elders: Boosting the Intelligence of Smart Homes," Am. Assoc. For Artificial Intell., (AAAI), Jul. 2002.

Dugan, U.S. Appl. No. 14/023,892, filed Sep. 11, 2013.

Dugan, U.S. Appl. No. 13/942,605, filed Jul. 15, 2013.

* cited by examiner

US 8,947,226 B2

BANDS FOR MEASURING BIOMETRIC INFORMATION

The present application claims priority from U.S. Provisional Patent Application Ser. No. 61/493,313, filed Jun. 3, 2011 and titled "BANDS FOR MEASURING BIOMETRICS", which is hereby incorporated by reference herein in its entirety for all purposes.

FIELD OF THE INVENTION

The present invention relates to biometric measurements, and more particularly to wearable bands that may be employed to measure biometric information.

BACKGROUND

Biofeedback devices such as portable heart rate monitoring (HRM) devices are commonly used in fitness related activities for weight loss, goal heart rate (HR) training, and general HR monitoring. Such devices may sometimes be employed by healthcare professionals for chronic and/or acute heart condition monitoring and/or diagnosis.

Portable HRMs and other monitoring devices typically are expensive, and in some cases are cost prohibitive for many consumers. A need exists for inexpensive and/or simplified monitoring systems.

SUMMARY

In some aspects, a system is provided that includes (1) a wrist band having one or more sensors that measure biometric data of a user wearing the band; and (2) a display on the band that displays a message based on biometric data measured by the band. The message indicates a heart rate zone of the user.

In some aspects, a system is provided that includes (1) a wrist band having one or more sensors that measure biometric data of a user wearing the band; and (2) a display on the band that displays a message based on biometric data measured by the band. The message indicates a stress level the user.

In some aspects, a system is provided that includes a wrist band having one or more sensors that measure biometric data of a user wearing the band. The wrist band adapted to (1) detect at least one of a handshake, a first bump and a high five of the user; and (2) share information with another user in response to the detection.

Numerous other aspects are provided, as are various methods, apparatus and computer program products for carrying out these and other aspects of the invention. Each computer program product may be carried by a medium readable by a computer (e.g., a carrier wave signal, a floppy disc, a hard drive, a random access memory, etc.).

Other features and aspects of the present invention will become more fully apparent from the following detailed description, the appended claims, and the accompanying drawings.

DETAILED DESCRIPTION

In one or more embodiments of the invention, a wearable wrist band or "bracelet" (collectively referred to as a band herein) is provided that includes a sensor for measuring heart rate, pulse, temperature, or the like and displaying an indication of the measured data such as (1) a color; and/or (2) a message, which may depend on the value of the measured data. Examples include, for example:

(1) a stress level band having a color and/or message based on a measured stress level of a person wearing the band (e.g., as determined by measuring and/or monitoring heart rate, pulse rate, body temperature, perspiration, or the like); and/or
(2) a zone band having a color and/or message based on a determined heart rate zone of a person wearing the band (e.g., recovery, fat burning, target heart rate, anaerobic zone, maximum, etc.).

In some embodiments, the bands may be flexible and/or waterproof. Such bands are simple to use and inexpensive. Example embodiments are these and other bands are described below.

Figure 1A:
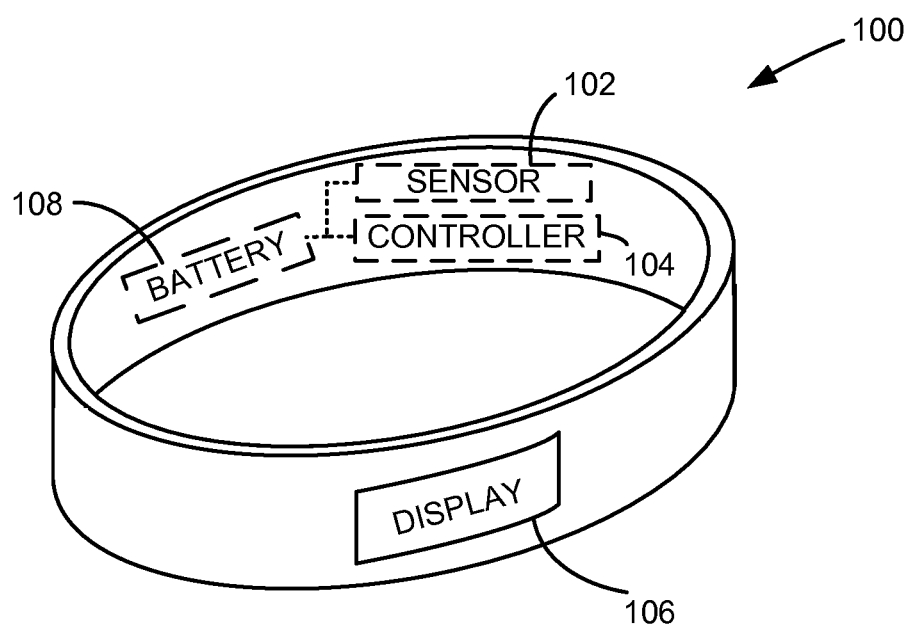
FIG. 1A is a schematic diagram of a band provided in accordance with the present invention.

FIG. 1A is a schematic diagram of a band 100 provided in accordance with the present invention. The band 100 may include a biometric sensor 102 coupled to a controller 104, and display 106 coupled to the controller 104. The band 100 may be fabricated from any suitable material. In some embodiments, the band 100 may be formed from a flexible and/or waterproof material such as silicone; and the sensor 102 and/or controller 104 may be embedded therein.

The sensor 102 may include any suitable biometric sensor configured to measure one or more of but is not limited to, heart rate, pulse rate, temperature, respiration, acceleration, skin resistivity, etc. More than one sensor 102 may be provided.

The controller 104 may include a programmable logic controller, microprocessor, application specific integrated circuit, or the like having suitable programming code for performing the methods described herein. More than one controller 104 may be used.

The display 106 may be any suitable display such as a liquid crystal display, electronic paper display, organic light-emitting diode display, or the like.

A battery 108 may be provided for powering sensor 102, controller 104 and/or display 106. In some embodiments, battery 108 may be rechargeable and/or replaceable. In one particular embodiment, the battery may be recharged via a USB connection (not shown) that allows information to be transferred from band 100 to another device such as a computer (not shown).

Figure 1B:
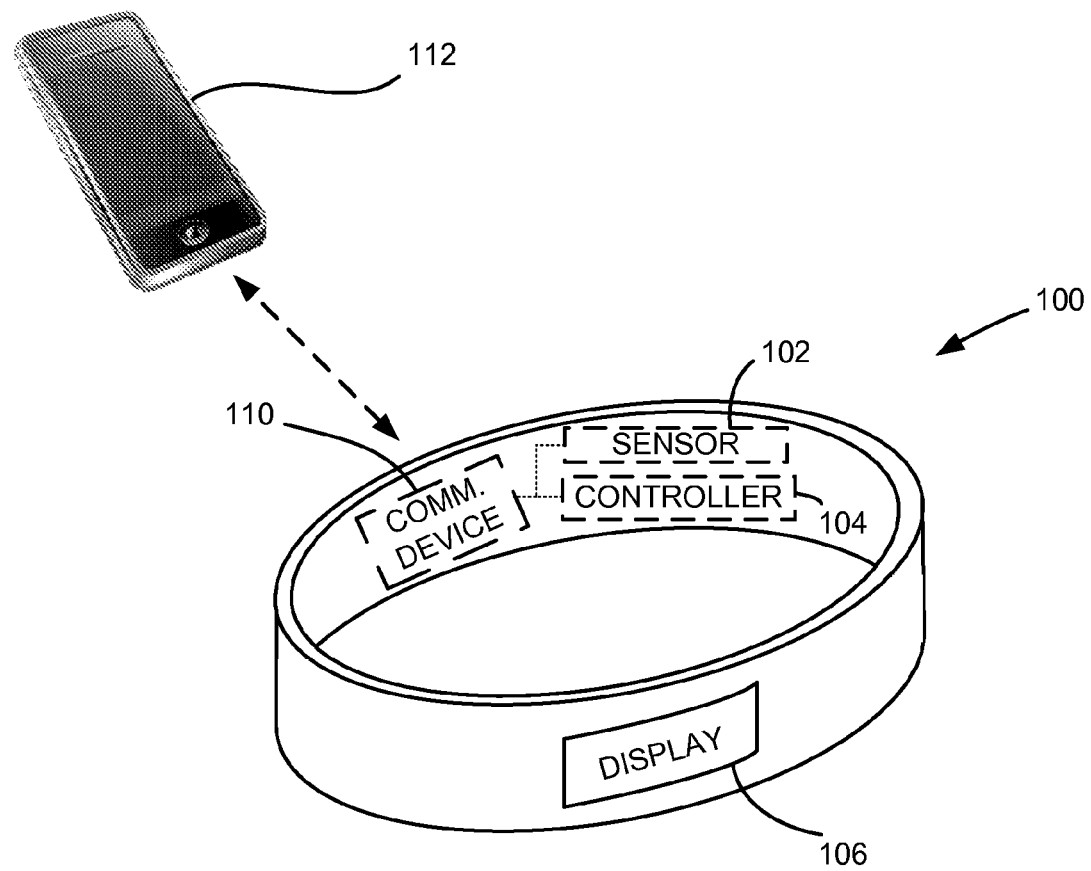
FIG. 1B illustrates an embodiment of the band of FIG. 1A that includes a communications device in accordance with the present invention.

In some embodiments, the band 100 may configured to communicate wirelessly with other devices such as a mobile telephone, tablet computer, laptop computer, desktop computer or the like. For example, FIG. 1B illustrates an embodiment of the band 100 in which the band 100 includes communications device 110 such as a transmitter/receiver chip that allows the controller 104 to communicate with a mobile device 112. In some embodiments, the controller 104 may send information to and/or receive information from mobile device 112 using a wireless protocol such as WiFi, Bluetooth, or the like.

Figure 2:
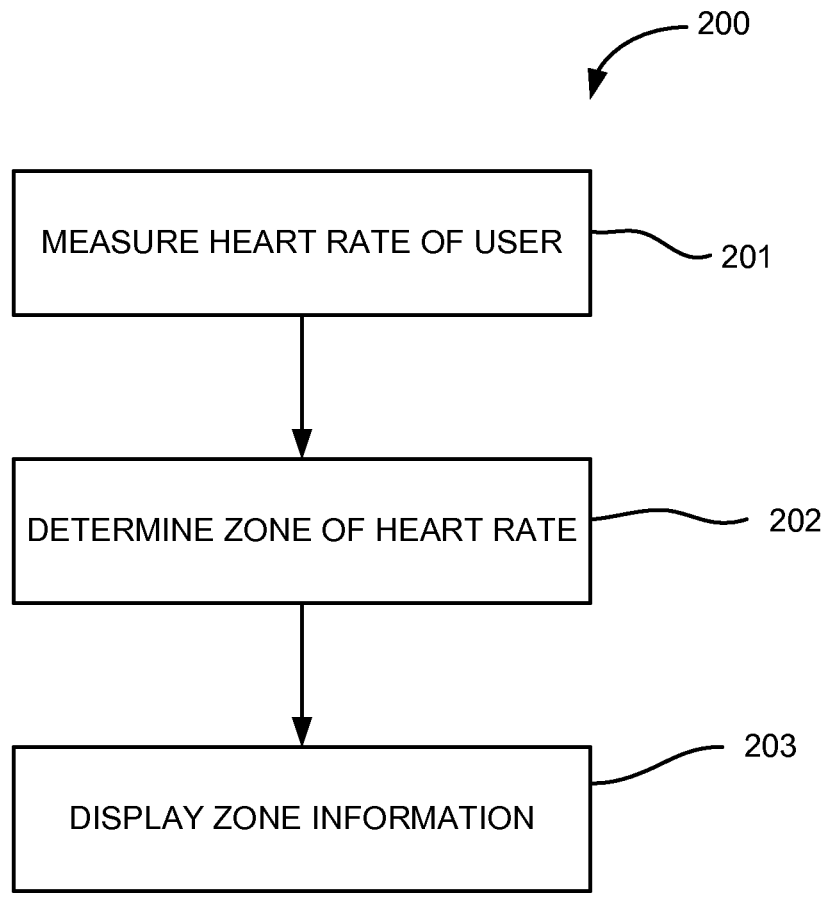
FIG. 2 is a flowchart of an example method of employing the band of FIGS. 1A and/or 1B for zone training in accordance with the present invention.

FIG. 2 is a flowchart of an example method 200 of employing the band 100 for zone training. With reference to FIGS. 1A-2, an exerciser (not shown) may wear the band 100 on his/her wrist. In step 201, sensor 102 of band 100 detects and measures the heart rate, pulse or another biometric parameter of the exerciser and provides this information to controller 104.

Based on the measured heart (or other information), in step 202, the controller 104 may determine an exercise zone for the exerciser. Generally, recommended exercise zones may depend on such factors as age and/or weight. In some embodiments, band 100 may be pre-programmed with particular definitions of the target heart rates for multiple zones. Any number of zones may be used (e.g., 1, 2, 3, 4, 5, 6, 7, etc.). For instance, bands may be pre-programmed with suitable heart rate zones for exercisers based on age and/or weight. In other embodiments, an exerciser may specify his/her age and/or weight and controller 104 may determine appropriate heart rate zones for the exerciser. For example, a mobile device 112 may include an application that prompts an exerciser for his/her age and/or weight, and then communicates this information (or zone information calculated by the mobile device) to the controller 104 via communications device 110.

In step 203, the band 100 displays heart rate zone information. For example, the controller 104 may cause display 106 to display a different color for each heart rate zone. In some embodiments, text information may be provided such as heart rate, zone, encouraging messages and/or warnings, or the like. Table 1 below provides exemplary colors for heart rate zones. Other colors may be employed.

TABLE 1

| HEART RATE RANGE (BEATS PER MINUTE) | COLOR |
|---|---|
| 70-95 | GREEN |
| 95-105 | BLUE |
| 105-120 | PURPLE |
| 120-135 | YELLOW |
| 135-150 | PINK |
| 150+ | RED |

In at least one embodiment, the controller 104 may include exercise routines that specify which heart rate zones an exerciser should be in and/or move between during an exercise routine. Band 100 may display an up arrow or down arrow (or other indicators) to indicate that an exerciser should increase or decrease his/her heart rate so as to move to another zone. A zone band may have a color and/or message based on what zone a user's heart rate is in (e.g., recovery, fat burning, target heart rate, or anaerobic zone). A different color can correspond to each zone, and/or the band 100 may display the current zone as a message.

Figure 3:
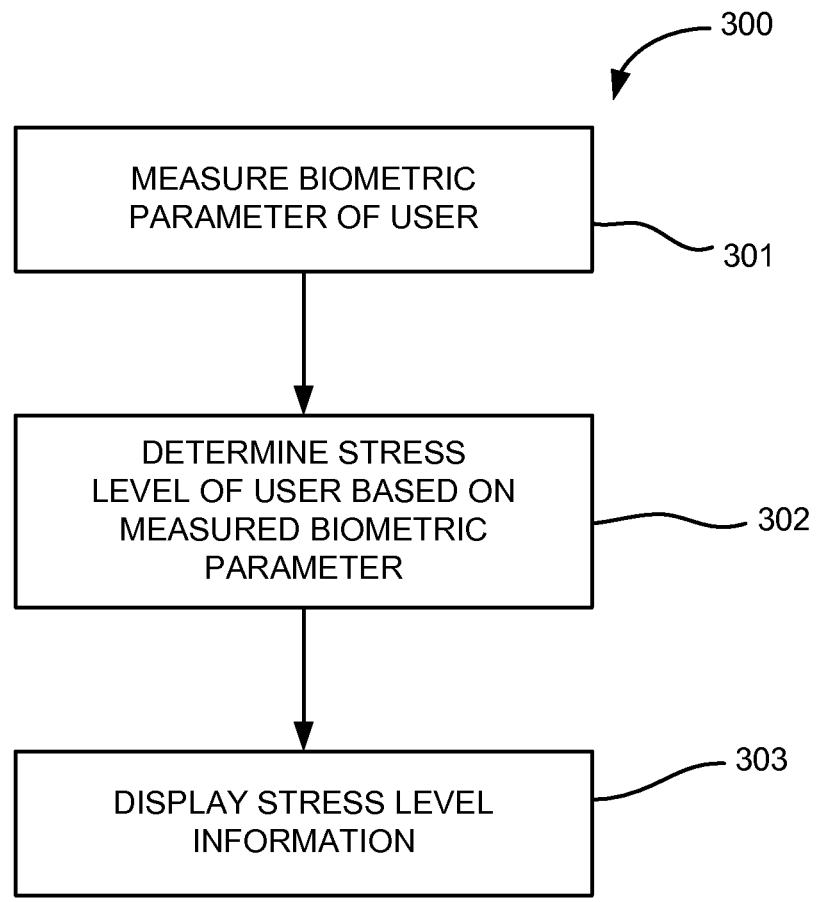
FIG. 3 is a flowchart of an example method of employing the band of FIG. 1A and/or 1B for monitoring stress level in accordance with the present invention.

FIG. 3 is a flowchart of an example method 300 of employing the band 100 for monitoring stress level in accordance with the present invention. With reference to FIGS. 1A-1B and FIG. 3, a user (not shown) may wear the band 100 on his/her wrist. In step 301, sensor 102 of band 100 detects and measures the heart rate, pulse or other biometric parameter of the user and provides this information to controller 104.

Based on the measured heart rate (or other parameter such as temperature), in step 302, the controller 104 may determine a stress level of the user. In general, heart rate increases as stress level increases. As such, controller 104 may determine when the heart rate of the user rises above a pre-determined heart rate level (e.g., such as a steady state heart rate for the user, or a heart rate measured when the user is relaxed). Zones of stress may be determined for the user such as low stress, moderate stress, high stress and extreme stress based on various heart rate ranges of the user. Temperature of the user may be similarly employed (e.g., as temperature may decrease with stress). Such stress ranges may be pre-programmed, determined by the controller 104, determined by mobile device 112 and communicated to controller 104 or the like. For example, a mobile device 112 may include an application that prompts the user to meditate, breath deep or otherwise relax when determining a low stress level for the user. The mobile application may then communicates this information (or zone information calculated by the mobile device) to the controller 104 via communications device 110.

In step 303, the band 100 displays stress level information for the user. For example, the controller 104 may cause display 106 to display a different color for each stress level zone of the user. In some embodiments, text information may be included such as heart rate, stress level zone, encouraging messages and/or warnings, or the like. Table 2 below provides example colors for stress level zones. Other colors may be employed.

TABLE 2

| STRESS LEVEL | COLOR |
|---|---|
| LOW | GREEN |
| MEDIUM | BLUE |
| HIGH | PURPLE |
| EXTREME | RED |

In at least one embodiment, the controller 104 may cause messages to be displayed on the display 106 such as "relax", "breathe", "getting agitated", "step away from the situation", or the like based on the level of stress of the user. In some embodiments, a stress level band may have a color and/or message based on stress level (e.g., as determined by heart rate, pulse, temperature, etc.). A user may use mind control to adjust your heart rate and change the message (e.g., via breathing techniques). Any suitable message may displayed such as be calm, back off, getting agitated, etc.

In some embodiments, the band 100 may be a "mood" band. For example, sensor 102 may measure temperature of a user and provide the temperature information to the controller 104. In response to this information, the controller 102 may cause display 106 to display a color representative of the user's mood. Example colors are provided below in Table 3. Other colors may be employed.

TABLE 3

| MOOD | COLOR |
|---|---|
| HAPPY/PASSIONATE | DARK BLUE |
| CALM | BLUE |
| SLIGHTLY CALM | BLUE GREEN |
| NORMAL | GREEN |
| SLIGHTLY NERVOUS | AMBER |
| ANXIOUS | GRAY |
| STRESSED | BLACK |

The temperature ranges used for each mood/color may be pre-selected based on statistical averages for men, women, boys, girls, etc., or in some embodiments, may be determined by the controller 104 by monitoring the steady state or normal temperature of a user and/or the temperature of the user during known times of stress. For example, mobile device 112 may include an application that asks a user his/her mood. Based on this information, the mobile device 112 may direct the controller 102 to store relevant temperature ranges which correlate to moods of the user. Of course, if desired, a mood band may be formed using thermotropic liquid crystals calibrated to a nominal temperature of about 82° F. as in a conventional mood ring in place of or in addition to the above described controller embodiment.

Figure 4:
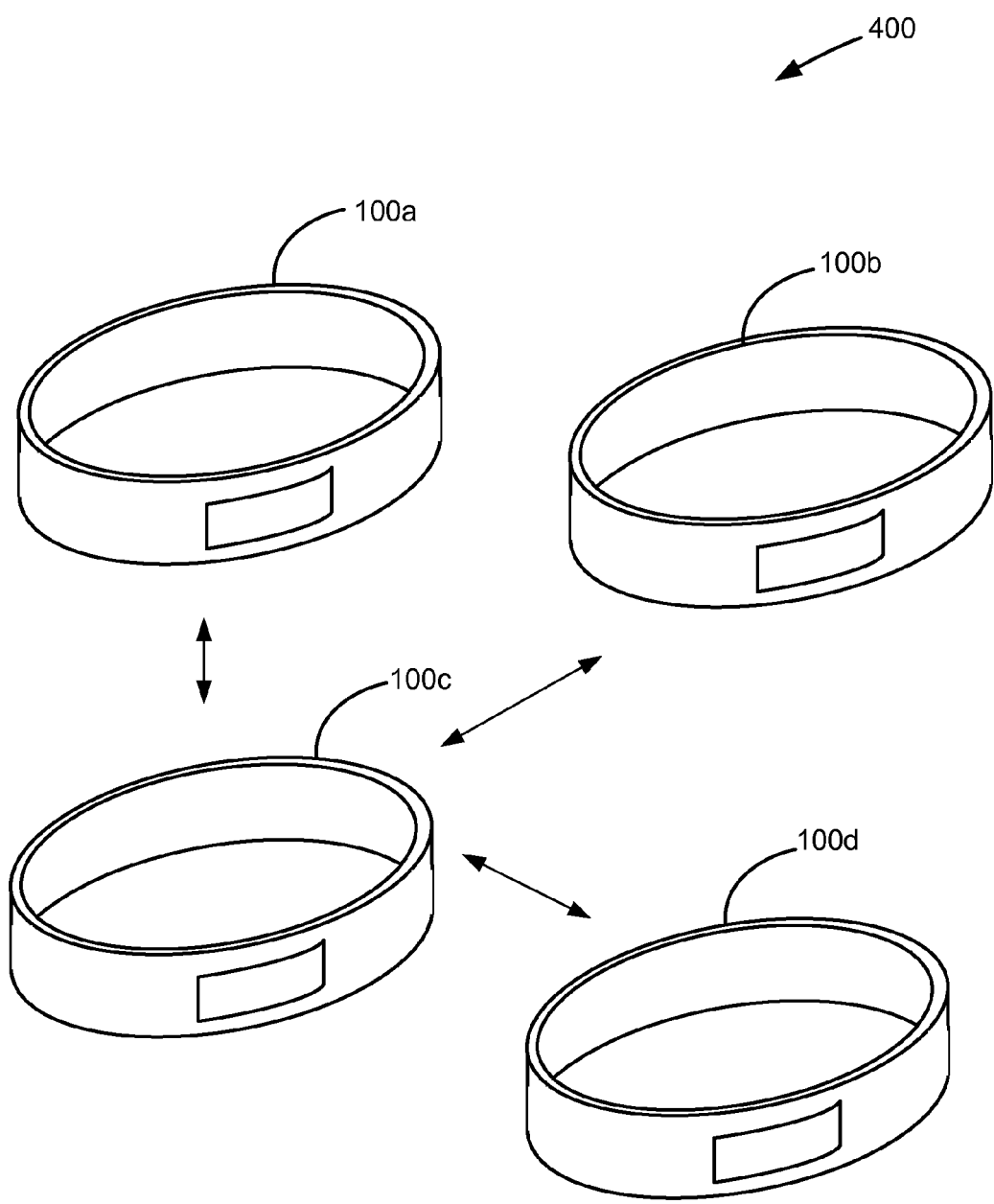
FIG. 4 illustrates a group that may be formed by a plurality of users employing bands in accordance with the present invention.

In some embodiments, the band 100 may be configured to detect the presence of like bands. For example, a band 100a may be assigned to a group 400 of bands 100a-d as shown in FIG. 4. Fewer or more bands may be in the group 400. Each band 100a in the group 400 may be configured to communicate with other bands in the group 400 (e.g., via communications device 110 and/or mobile device 112) so as to identify members of the group, such as to beep, vibrate, change colors and/or display a message when other people/members of group 400 are near (e.g., other people from your college, people with similar interest or status, people within a frequent flyer program or points level, etc.), or the like. For instance, each band 100a-d may periodically broadcast identifying information so that any band in the group 400 may detect and identify the band(s).

In some embodiments, bands 100 may "exchange" information with other bands in a group or any other band. For instance, the sensor 102 may include an accelerometer (not separately shown) that may recognize a handshake by a user of the band (e.g., by detecting the rapid up/down motion which occurs when two people shake hands). This may trigger the controller 104 in the band 100 of each person to share contact information for the user (e.g., email addresses, cellular telephone numbers, generate a Facebook friend request, or the like). Likewise, bands may be "bumped" together to share information. Any such information may be communicated to mobile devices 112 if desired. As an example, person A wearing band 100a may shake hands, high five, bump fists, etc., with person B wearing band 100b. Each band 100a, 100b may include a sensor 102 such as an accelerometer, strain gauge or the like which detects an acceleration and/or an acceleration pattern along one or more axis that is identifiable by controller 104 of each band 100a, 100b as a request to share information. In response thereto, controller 104 of each band 100a, 100b may cause information to be shared. For instance, bands 100a, 100b may directly broadcast information between one another; and/or bands 100a, 100b may direct mobile devices 112 of each user to share contact or other information.

In other embodiments, a wearable band may include a built in flash drive in place of or in addition to one or more the above. For example, monitored/collected data may be stored on the flash drive.

In one or more embodiments, a band may be used to motivate people to take the stairs. Most staircases in buildings are stark and depressing. A hotel chain may spruce of their staircases and even provide incentives for people to use them (to promote healthy living, save electricity by not using elevators, etc.). One or more of the above bands may be used as part of such a promotions.

Accordingly, while the present invention has been disclosed in connection with exemplary embodiments thereof, it should be understood that other embodiments may fall within the spirit and scope of the invention, as defined by the following claims.

The invention claimed is:

1. A system comprising:
a first wrist band having one or more sensors that measure biometric data of a first user wearing the first band, the first wrist band adapted to:
detect proximity to a second user wearing a second wrist band;
detect at least one of a handshake, a fist bump and a high five occurring between the first and second users; and
share information between the first and second users in response to the detection of the handshake, fist bump, or high five,
wherein the first wrist band is further adapted to determine if the second user is a member of a group associated with the first user and to display a color indicating the group association;
wherein the first wrist band is adapted to communicate with a mobile device of the first user and the second wrist band is adapted to communicate with a mobile device of the second user, and
wherein the sharing of information between the first and second users in response to the detection of the handshake, fist bump, or high five occurs directly between the mobile devices of the first and second users.

2. The system of claim 1 wherein the first wrist band is flexible.

3. The system of claim 1 wherein the first wrist band includes an acceleration sensor for detecting a handshake, a fist bump or a high five.

4. The system of claim 1 wherein the first wrist band includes an accelerometer.

5. The system of claim 1 wherein the first wrist band is adapted to communicate with the second wrist band to share the information.

6. The system of claim 1 wherein the information shared includes contact information.

7. The system of claim 1 wherein the information shared includes monitored or collected data.

8. The system of claim 1 wherein the first wrist band includes a flash drive.

9. The system of claim 8 wherein the information shared includes data stored on the flash drive.

10. The system of claim 1 wherein the first wrist band is further adapted to emit a sound or vibration or display a message indicating the presence of the second user who is a member of the group associated with the first user.

11. A system comprising:
a mobile device of a first user; and
a first wrist band having one or more sensors configured to measure biometric data of the first user, the first wrist band operative to communicate measured biometric data to the mobile device of the first user, the first wrist band and the mobile device of the first user operative to:
detect proximity to a second user wearing a second wrist band, the second wrist band being adapted to communicate with a mobile device of the second user;
detect at least one of a handshake, a fist bump and a high five occurring between the first and second users based on communication from the first wrist band; and
share information between the first and second users in response to the detection of the handshake, fist bump, or high five; and
wherein the sharing of information between the first and second users in response to the detection of the handshake, fist bump, or high five includes sharing of information between the mobile devices of the first and second users.

12. The system of claim 11 wherein the first wrist band is flexible.

13. The system of claim 11 wherein the first wrist band includes an acceleration sensor for detecting a handshake, a fist bump or a high five.

14. The system of claim 11 wherein the information shared includes contact information.

15. The system of claim 11 wherein the information shared includes monitored or collected data.

16. The system of claim 11 wherein the first wrist band includes a flash drive.

17. The system of claim 16 wherein the information shared includes data stored on the flash drive.

18. The system of claim 11 wherein the first wrist band is further adapted to emit a sound or vibration or display a message indicating the presence of the second user if the second user is a member of a group associated with the first user.

19. The system of claim 11 wherein the first wrist band is adapted to display a color corresponding to a heart rate zone of the first user.

20. The system of claim 11 wherein the first wrist band is adapted to display a color corresponding to a stress level of the user.

21. The system of claim 1 wherein the sharing of information between the first and second users includes generating a social network friend request.

22. The system of claim 11 wherein the sharing of information between the first and second users includes generating a social network friend request.

* * * * *